US012590864B2

(12) United States Patent
Richards et al.

(10) Patent No.: US 12,590,864 B2
(45) Date of Patent: Mar. 31, 2026

(54) WIND TUNNEL FOR ASSESSMENT OF INSECTICIDES

(71) Applicant: EAST CAROLINA UNIVERSITY, Greenville, NC (US)

(72) Inventors: Stephanie Lynn Richards, Winterville, NC (US); Sinan Sousan, Greenville, NC (US)

(73) Assignee: EAST CAROLINA UNIVERSITY, Greenville, NC (US)

( * ) Notice: Subject to any disclaimer, the term of this patent is extended or adjusted under 35 U.S.C. 154(b) by 0 days.

(21) Appl. No.: 19/306,274

(22) Filed: Aug. 21, 2025

(65) Prior Publication Data

US 2025/0389613 A1 Dec. 25, 2025

Related U.S. Application Data

(63) Continuation of application No. PCT/US2024/049971, filed on Oct. 4, 2024.
(Continued)

(51) Int. Cl.
*A01M 7/00* (2006.01)
*G01M 9/04* (2006.01)
*G01N 33/00* (2006.01)

(52) U.S. Cl.
CPC ............ *G01M 9/04* (2013.01); *A01M 7/0089* (2013.01); *G01N 33/0036* (2013.01)

(58) Field of Classification Search
CPC . A01M 7/0089; A01M 7/0003; A01M 7/0014
See application file for complete search history.

(56) References Cited

U.S. PATENT DOCUMENTS 3,269,657 A * 8/1966 Ballu .................. A01M 7/0014
239/DIG. 21
2016/0334319 A1* 11/2016 Lindner ............. G01N 15/0227
(Continued)

FOREIGN PATENT DOCUMENTS

CN 111442898 A * 7/2020 .............. G01M 9/02
CN 219657125 U 9/2023
(Continued)

OTHER PUBLICATIONS

International Search Report and Written Opinion corresponding to PCT/US2024/049971; Mailed: Jan. 8, 2025, (12 pp).
(Continued)

*Primary Examiner* — Christopher P Ellis
(74) *Attorney, Agent, or Firm* — Myers Bigel, P.A.

(57) ABSTRACT

A wind tunnel system is configured to assess insecticides. The system includes: a chamber having an inlet configured to receive a gas flowing into the chamber and an outlet configured to output the gas from the chamber; an inlet filter configured to filter the gas flowing into the chamber; an outlet filter configured to filter the gas flowing out of the chamber; an aerosol generator configured to generate an insecticide aerosol downstream from the inlet filter; an insect container holder configured to secure an insect container in the chamber downstream from the aerosol generator and upstream from the outlet filter; and an airflow controller configured to flow the gas into the inlet and out of the outlet of the chamber such that the insecticide aerosol flows through an insect container in the chamber.

21 Claims, 9 Drawing Sheets

Related U.S. Application Data

(60) Provisional application No. 63/588,137, filed on Oct. 5, 2023.

(56) References Cited

U.S. PATENT DOCUMENTS

| | | | |
|---|---|---|---|
| 2019/0078970 A1 | 3/2019 | Hambleton et al. | |
| 2022/0011181 A1 | 1/2022 | Zhang et al. | |
| 2022/0283130 A1* | 9/2022 | Lane | H01J 49/0431 |

FOREIGN PATENT DOCUMENTS

| | | | | |
|---|---|---|---|---|
| WO | WO-2004036989 A1 * | 5/2004 | | A01M 1/06 |
| WO | WO-2018037253 A1 * | 3/2018 | | G01N 15/02 |

OTHER PUBLICATIONS

Barber, et al., "Canopy Effects Droplet Size Distribution and Meteorological Change", Journal of the American Mosquito Control Association, 24(1), 2008, 177-181.

Bianco, et al., "Aerosol drug delivery to spontaneously-breathing preterm neonates: lessons learned", Respiratory Research, 22(1), 2021, 1-31.

Bonds, J. A. S., "Ultra-low-vol. space sprays in mosquito control: a critical review", Medical and Veterinary Entomology, 26(2), 2012, 121-130.

Brown, et al., "Operational Insights Into Mosquito Control Disaster Response in Coastal North Carolina: Experiences With the Federal Emergency Management Agency After Hurricane Florence", Journal of Environmental Health, 85(2), 2022, 24-31.

Burgess IV, et al., "Assessing pyrethroid resistance status in the Culex pipiens complex (Diptera: Culicidae) from the northwest suburbs of Chicago, Illinois using Cox regression of bottle bioassays and other detection tools", PLoS ONE, 17(6): e0268205, 2022, 1-17.

CDC, "CONUS Manual for Evaluating Insecticide Resistance in Mosquitoes Using the CDC Bottle Bioassay Kit", Division of Vector-Borne Diseases, Centers for Disease Control and Prevention (CDC), Mar. 2021, (19 pp).

CDC, "Guideline for Evaluating Insecticide Resistance in Vectors Using the CDC Bottle Bioassay", Division of Parasitic Diseases and Malaria, Centers for Disease Control and Prevention (CDC), 2013, (28 pp).

Chaaban, et al., "Assessment of best-selling respirators and masks: Do we have acceptable respiratory protection for the next pandemic? ", American Journal of Infection Control, 51(4), 2023, 388-395.

Cooperband, et al., "Prallethrin-Induced Excitation Increases Contact Between Sprayed Ultralow Volume Droplets and Flying Mosquitoes (Diptera: Culicidae) in a Wind Tunnel", Journal of Medical Entomology, 47(6), 2010, 1099-1106.

Danelli, et al., "Comparative characterization of the performance of bio-aerosol nebulizers in connection with atmospheric simulation chambers", Atmospheric Measurement Techniques, 14(6), 2021, 4461-4470.

Dekker, et al., "Moment-to-moment flight manoeuvres of the female yellow fever mosquito (*Aedes aegypti* L.) in response to plumes of carbon dioxide and human skin odour", Journal of Experimental Biology, 214(20), 2011, 3480-3494.

Dzul-Manzanilla, et al., "Field Efficacy Trials of Aerial Ultra-Low-vol. Application of Insecticides Against Caged Aedes aegypti in Mexico", Journal of the American Mosquito Control Association, 35(2), 2019, 140-146.

Finlay, et al., "Particle Size Distributions", Journal of Aerosol Medicine and Pulmonary Drug Delivery, 33(4), 2020, 178-180.

Fritz, et al., "Filtration Effects Due to Bioassay Cage Design and Screen Type", Journal of the American Mosquito Control Association, 26(4), 2010, 411-421.

Fritz, et al., "The biological effect of cage design corrected for reductions in spray penetration", Journal of Plant Protection Research, 54(4), 2014, 395-400.

Hinze, et al., "Mosquito Host Seeking in 3D Using a Versatile Climate-Controlled Wind Tunnel System", Frontiers in Behavioral Neuroscience, 15: 643693, 2021, 1-11.

Hoffmann, et al., "Droplet-Size Characterization of Handheld Atomization Equipment Typically Used in Vector Control", Journal of the American Mosquito Control Association, 23(3), 2007, 315-320.

Hoffmann, et al., "Effects of Wind Speed on Aerosol Spray Penetration in Adult Mosquito Bioassay Cages", Journal of the American Mosquito Control Association, 24(3), 2008, 419-426.

Lofgren, et al., "Size of Aerosol Droplets Impinging on Mosquitoes as Determined with a Scanning Electron Microscope", Journal of Economic Entomology, 66(5), 1973, 1085-1088.

Matthews, G.A. , "Determination of Droplet Size", PANS Pest Articles & News Summaries, 21(2), 1975, 213-225.

May, et al., "The Impaction of Aerosol Particles on Cylinders, Spheres, Ribbons and Discs", The Annals of Occupational Hygiene, 10(2), 1967, 83-95.

Mount, et al., "A review of ultralow-volume aerial sprays of insecticide for mosquito control", Journal of the American Mosquito Control Association, 12(4), 1996, 601-618.

Naccho, "Mosquito Control Capabilities in the U.S.", National Association of County and City Health Officials (NACCHO), Available: https://www.naccho.org/uploads/downloadable-resources/Mosquito-control-in-the-U.S.-Report. pdf, 2017, (25 pp).

PES, "Understanding Droplet Size", Pesticide Environmental Stewardship (PES) [Internet]. Available: https://pesticidestewardship.org/pesticide-drift/understanding-droplet-size/ [Accessed: Aug. 8, 2025; Available: 2019], 2019, (5 pp).

Richards, et al., "Assessing Insecticide Resistance in Adult Mosquitoes: Perspectives on Current Methods", Environmental Health Insights, 14, 2020, 1-7.

Richards, et al., "Baseline Insecticide Susceptibility Screening Against Six Active Ingredients for Culex and Aedes (Diptera: Culicidae) Mosquitoes in the United States", Journal of Medical Entomology, 54(3), 2017, 682-695.

Richards, et al., "Evaluation of Insecticide Resistance in Aedes albopictus (Diptera: Culicidae) in North Carolina, 2017", Journal of Medical Entomology, 56(3), 2019, 761-773.

Richards, et al., "Insecticide Susceptibility Screening Against Culex and Aedes (Diptera: Culicidae) Mosquitoes From the United States", Journal of Medical Entomology, 55(2), 2017, 398-407.

Richards, et al., "Survey of United States Mosquito Control Programs Reveals Opportunities to Improve the Operational Value of Centers for Disease Control and Prevention Bottle Bioassays", Journal of Medical Entomology, 59(5), 2022, 1827-1830.

Scheff, et al., "Case Study: A Practical Application of an Aerosol Treatment in a Commercial Mill", Insects, 10(5): 150, 2019.

Sousan, et al., "Laboratory Evaluation of Low-Cost Optical Particle Counters for Environmental and Occupational Exposures", Sensors, 21(12): 4146, 2021, 1-26.

Streuber, et al., "Laboratory and Field Evaluations of the GeoAir2 Air Quality Monitor for Use in Indoor Environments", Aerosol and Air Quality Research, 22(8): 220119, 2022, 1-14.

Tauxe, et al., "Targeting a Dual Detector of Skin and CO2 to Modify Mosquito Host Seeking", Cell, 155(6), 2013, 1365-1379.

Van Den Berg, et al., "Recent trends in global insecticide use for disease vector control and potential implications for resistance management", Scientific reports, 11(1): 23867, 2021, 1-12.

World Health Organization (WHO), "Global Vector Control Response 2017-2030", Response Plan published Oct. 2, 2017, (64 pp).

Zhang, et al., "Retention and efficacy of ultra-low volume pesticide applications on Culex quinquefasciatus (Diptera: Culicidae)", Environmental Science and Pollution Research, 22(21), 2015, 16492-16501.

* cited by examiner

WIND TUNNEL FOR ASSESSMENT OF INSECTICIDES

RELATED APPLICATIONS

This application is a bypass continuation of International Application No. PCT/US2024/049971, filed Oct. 4, 2024, which claims priority to U.S. Provisional Application Ser. No. 63/588,137, filed Oct. 5, 2023, the disclosures of which are incorporated herein by reference in their entirety.

STATEMENT OF GOVERNMENT SUPPORT

This invention was made with government support under NU50CK000384 awarded by the Centers for Disease Control and Prevention. The government has certain rights in the invention.

FIELD OF THE INVENTION

The present invention relates to wind tunnels for assessing insecticide, and in particular, to wind tunnels for assessing effectiveness and/or resistance of insecticides in insects such as mosquitoes.

SUMMARY

According to some embodiments, a wind tunnel system is configured to assess insecticides, the system includes: a chamber having an inlet configured to receive a gas flowing into the chamber and an outlet configured to output the gas from the chamber; an inlet filter configured to filter the gas flowing into the chamber; an outlet filter configured to filter the gas flowing out of the chamber; an aerosol generator configured to generate an insecticide aerosol downstream from the inlet filter; an insect container holder configured to secure an insect container in the chamber downstream from the aerosol generator and upstream from the outlet filter; and an airflow controller configured to flow the gas into the inlet and out of the outlet of the chamber such that the insecticide aerosol flows through an insect container in the chamber.

In some embodiments, a method of assessing insecticide with a wind tunnel system includes providing a wind tunnel system comprising: a chamber having an inlet configured to receive a gas flowing into the chamber and an outlet configured to output the gas from the chamber; an inlet filter configured to filter the gas flowing into the chamber; an outlet filter configured to filter the gas flowing out of the chamber; an aerosol generator configured to generate an insecticide aerosol downstream from the inlet filter; an insect container holder configured to secure an insect container in the chamber downstream from the aerosol generator and upstream from the outlet filter; and an airflow controller configured to flow the gas into the inlet and out of the outlet of the chamber; connecting an insect container to the insect container holder, the insect container comprising a gas permeable sidewall configured to allow the gas to flow through the insect container; aerosolizing insecticide in the chamber; and flowing gas through the inlet and out of the outlet of the chamber such that the insecticide aerosol flows through an insect container in the chamber.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 2, panel B, is a front perspective view of the wind tunnel system of FIG. 2, panel A, with a front sidewall removed.

FIG. 2, panels C-D, are back perspective views of the wind tunnel of FIG. 2, panel A, with a back sidewall removed.

DETAILED DESCRIPTION

Figure 1:
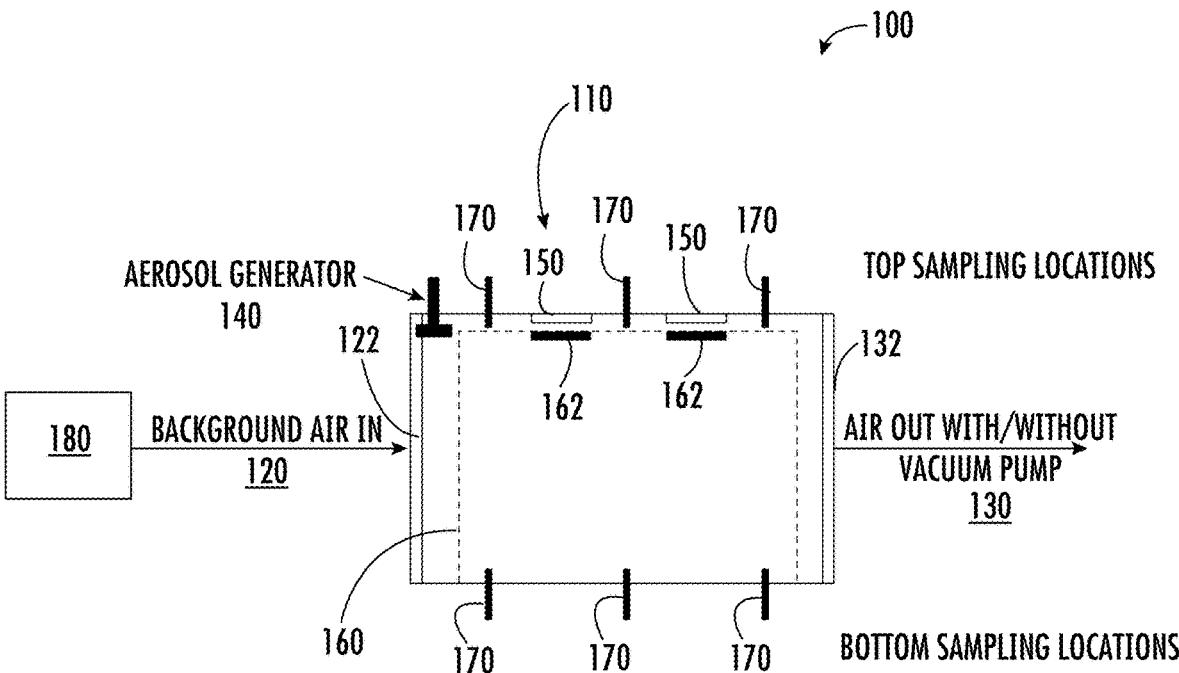
FIG. 1 is a side schematic view of a wind tunnel system according to some embodiments.

The present inventive concepts are described herein with reference to the accompanying drawings and examples, in which embodiments are shown. Additional embodiments may take on many different forms and should not be construed as limited to the embodiments set forth herein. Rather, these embodiments are provided so that this disclosure will be thorough and complete, and will fully convey the scope of the inventive concepts to those skilled in the art.

The terminology used herein is for the purpose of describing particular embodiments only and is not intended to be limiting thereof. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims, description, or figures unless specifically indicated otherwise.

The present invention is described herein with reference to operations that can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts described herein.

These computer program instructions may also be stored in a computer-readable memory that can direct a computer or other programmable data processing apparatus to function in a particular manner, such that the instructions stored in the computer-readable memory produce an article of manufacture including instructions which implement the function/act described herein.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts described herein.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

Mosquitoes can develop resistance to insecticide active ingredients (AI) over time. Mosquito exposure to insecticides during ultra-low volume (ULV) application occurs via direct liquid contact with formulated products (FP), while barrier applications expose mosquitoes to residual FP. The Centers for Disease Control and Prevention (CDC) bottle bioassay is based on contact with residual insecticide AI. The CDC bottle bioassay does not directly relate to operational interventions for ULV applications of FP that have additional ingredients that may enhance effectiveness.

As illustrated in FIG. 1, a wind tunnel system 100 is configured to assess insecticides in insects in the wind tunnel system 100. The wind tunnel system 100 includes a chamber 110 having an inlet 120 configured to receive a gas flowing into the chamber 110 and an outlet 130 configured to output a gas from the chamber 110. An inlet filter 122 is configured to filter gas into the chamber 110, and an outlet filter 132 is configured to filter gas flowing out of the chamber 110. An aerosol generator 140 is configured to generate an insecticide aerosol downstream from the outlet filter 132. An insect container holder 150 (such as a magnet) is configured to secure an insect container 160 in the chamber downstream from the aerosol generator 140 and upstream from the outlet filter 132. An airflow controller 180, such as a blower, fan, mass flow controller, or vacuum pump, is configured to flow the gas into the inlet 120 and out of the outlet 130 so that the insecticide aerosol flows through the insect container in the chamber 110. Aerosol sampling devices 170 are positioned in the chamber 110 and are configured to sample the gas in the chamber 110 and/or to characterize the aerosol or insecticide generated by the aerosol generator 140.

For example, the aerosol generator 140 may be a nebulizer or atomizer that is configured to aerosolize liquids in solutions. The aerosol sampling devices 170 may be optionally added to determine or verify the droplet size or volume median diameter (VMD) or mass median diameter (MMD) of the droplets.

Figure 5:
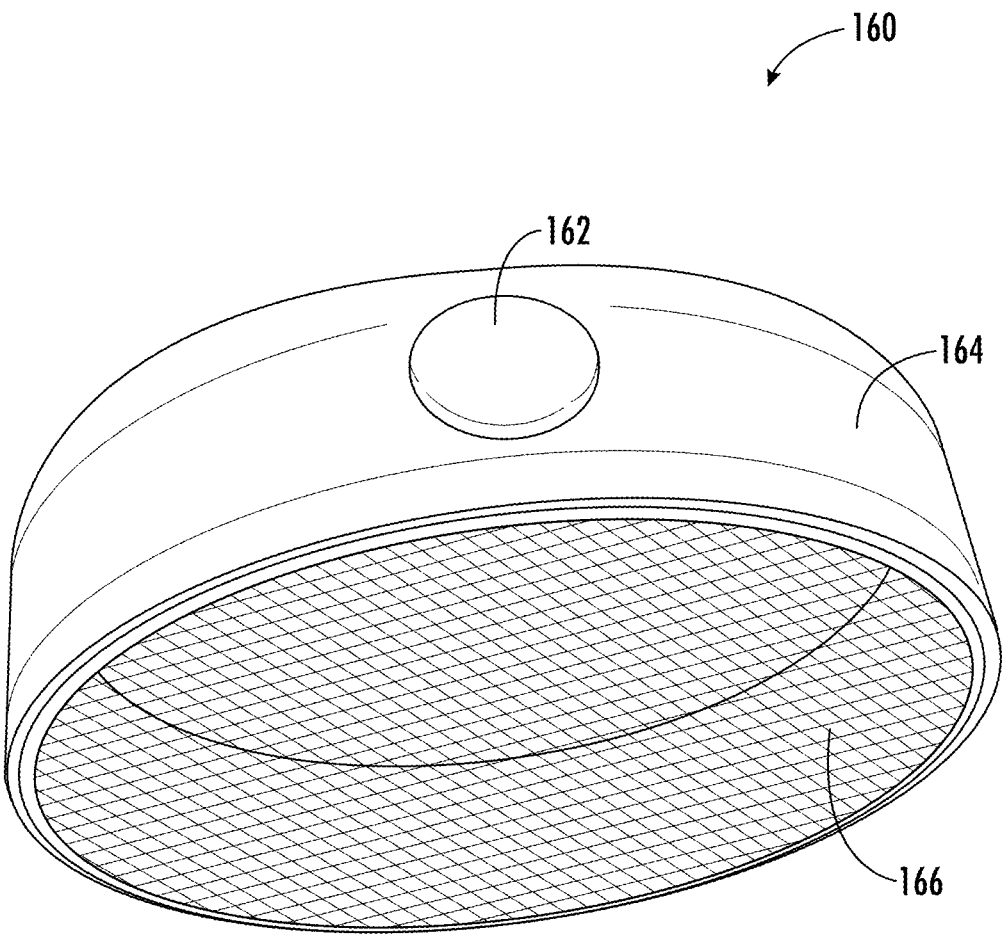
FIG. 5 is a mosquito container for use with the wind tunnel systems of FIGS. 1-3.

As shown in FIG. 5, the insect container 160 includes a magnet 162 on a sidewall 164. Front and back sidewalls 166 may be formed of a permeable material, such as netting or other material that has apertures for airflow that are not sufficiently large for the insects, such as mosquitoes, to escape from the interior of the container 160. The insects may be added to the container 160 through an aperture that can be opened or closed on the sidewall 164 or other suitable entryway into the interior of the container 160. The sidewall 164 may be a solid sidewall formed of any suitable material, such as polyvinyl chloride (PVC), metal, elastomers, etc.

As illustrated in FIG. 1, the chamber 110 includes holders 150 for holding the insect container 160. In particular, the holders 150 are magnets positioned on an interior sidewall of the chamber 110 that magnetically couple with corresponding magnets 162 on the side of the insect container 160. However, any suitable holders for holding the insect container 160 may be used, including hooks, hook and loop configurations, ties, and the like. In some embodiments, the insect container 160 is held in position so that it does not change orientation during flow of gas or air through the chamber 110.

In this configuration, a population of insects may be introduced into the interior chamber of the insect container 160 and positioned into the chamber 110. An insecticide is aerosolized by the aerosol generator 140 as air is flowed through the chamber 110 by the airflow controller 180 through the inlet 120 and outlet 130. After a period of time, the inflow through the chamber 110 is ceased and the insect container 160 is removed from the chamber 110. The number of live and dead insects are assessed to determine the efficacy of the insecticide.

The wind tunnel system 100 may be sufficiently small so as to fit under a chemical hood or vent in a lab setting. For example, the chamber 110 may be less than one foot long and less than seven inches tall. However, any suitable dimensions may be used, such as between about one foot long to three feet long or more and six inches tall to one foot tall or more.

The filters 122 and 132 at the inlet 120 and outlet 130, respectively, may reduce or eliminate the exposure of insecticide outside of the chamber 110. The filters 122 and 132 may be HEPA filters. When the chamber 110 is further placed under a chemical hood or vent, the exposure of insecticides during testing is reduced or eliminated.

Therefore, different insecticides may be tested in different insect populations to determine how much or whether to use the insecticide in a given environment. Embodiments according to the inventive concept may be used to assess insecticides for a mosquito insect population; however, other insects may be tested in the wind tunnel system 100, including any flying (examples include but are not limited to flies such as sand flies, house flies, blow flies, deer flies, fruit flies) or crawling (examples include but are not limited to beetles, ants, cockroaches, bed bugs, aphids) insect, arachnids (examples include but are not limited to ticks, mites, spiders), or other pests. In some embodiments, testing for desirable insects may be performed, such as pollinators.

Figure 2:
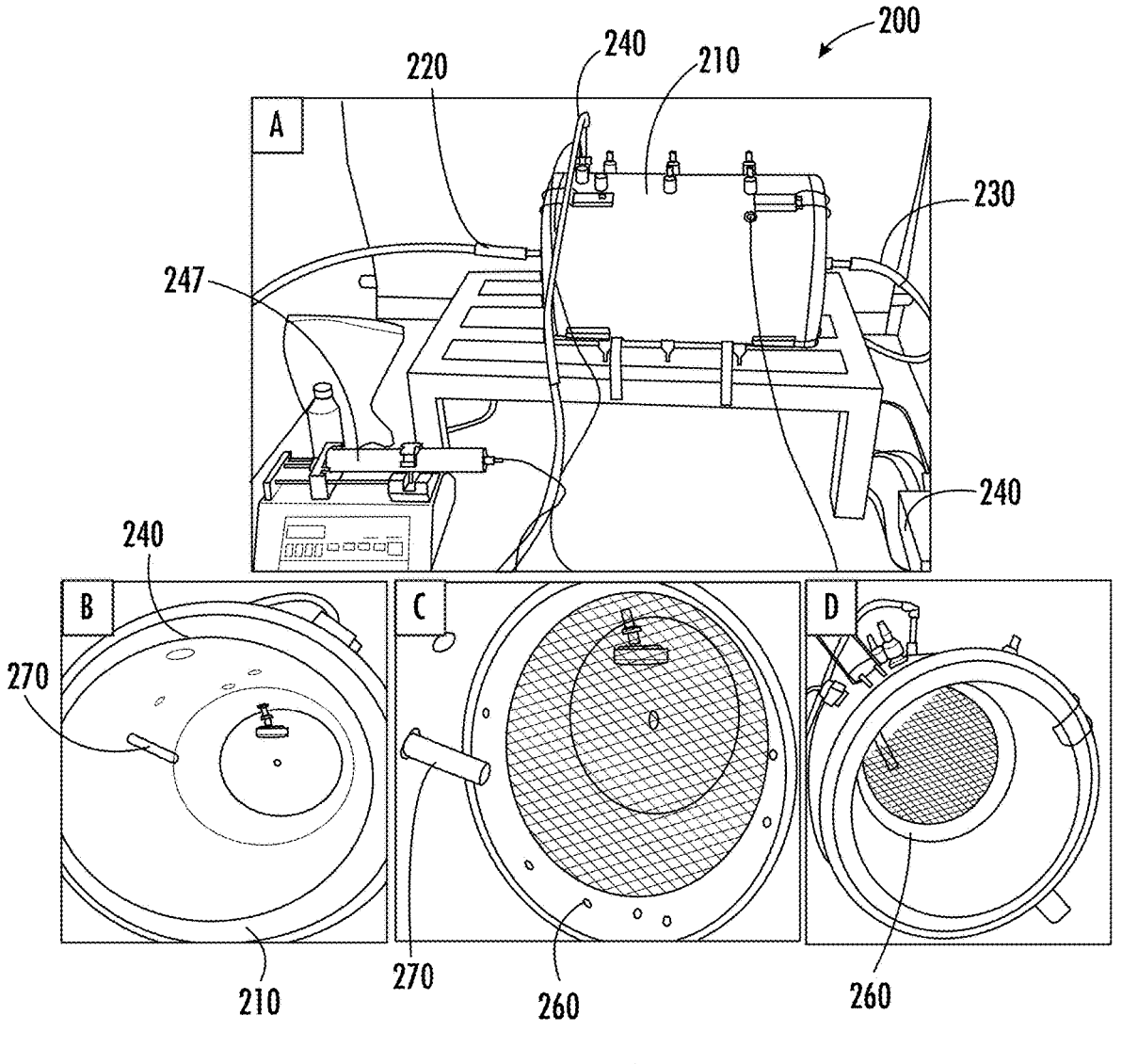
FIG. 2, panel A, is a side perspective view of a wind tunnel system according to some embodiments.

A wind tunnel system 200 is illustrated in FIG. 2, panels A-D, in which a chamber 210 includes a gas inlet 220 and outlet 230, and aerosol generator 240 connected to a liquid syringe pump 247, an aerosol sampling device 270, and an insect container 262. The insecticide may be added to the liquid syringe pump 247 and aerosolized by the aerosol sampling device. A mass flow controller and vacuum pump may be configured to flow gas, such as air, from the inlet 220 to the outlet 230. Inlet and outlet filters may be used to provide clean air to the chamber 210 and to reduce or eliminate insecticide from exiting the chamber 210.

Figure 4:
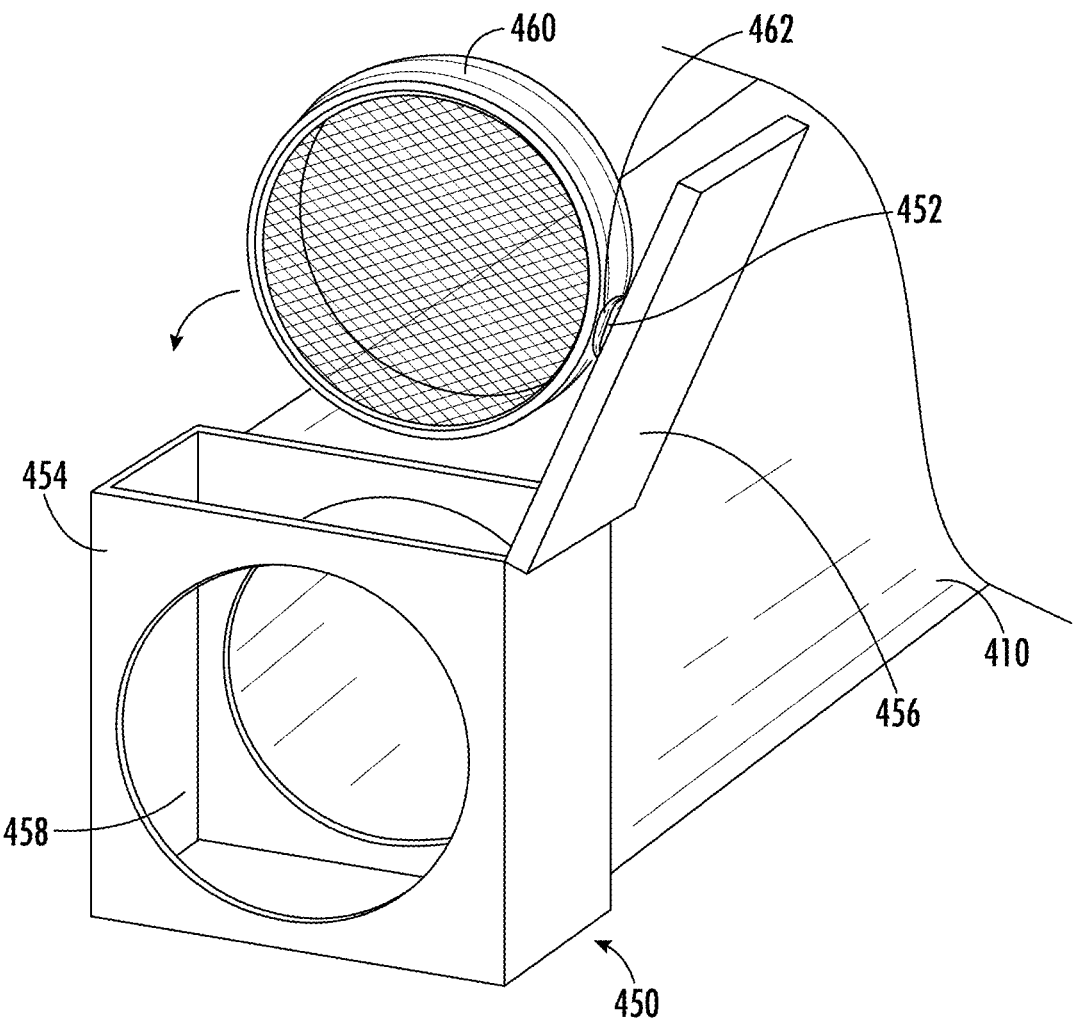
FIG. 4 is a perspective view of an insect container holder of the wind tunnel system of FIG. 3.

As shown in FIG. 4, a wind tunnel system 400 includes a chamber 410 having an inlet 420 configured to receive a gas flowing into the chamber 410 and an outlet 430 configured to output a gas from the chamber 410. An inlet filter 422 is configured to filter gas into the chamber 410, and an outlet filter 432 is configured to filter gas flowing out of the chamber 410. An aerosol generator 440 is configured to generate an insecticide aerosol downstream from the outlet filter 432. An insect container holder 450 is configured to secure an insect container 460 in the chamber downstream from the aerosol generator 440 and upstream from the outlet filter 432. An airflow controller or blower 480 is downstream of the filter 432 and is configured to blow the gas out of the outlet 430 and to create a negative pressure that flows air or gas into the inlet 420 and out of the outlet 430. In this configuration, gas flows through the chamber 410 so that the insecticide aerosol flows through the insect container 460 in the chamber 410. Aerosol sampling devices 470 may also be included in the chamber 410 as described with respect to FIG. 1.

As illustrated, the aerosol generator 440 includes a compressed air source 441 downstream from an oil trap 442, valve 443, gas regulator, 444, diffusion dryer 445 and HEPA filter 446, which together flows a controlled stream of clean air into an atomizer 448. A syringe pump 447 is configured to flow the insecticide into the atomizer 448, where it is introduced into the chamber 410.

Figure 3:
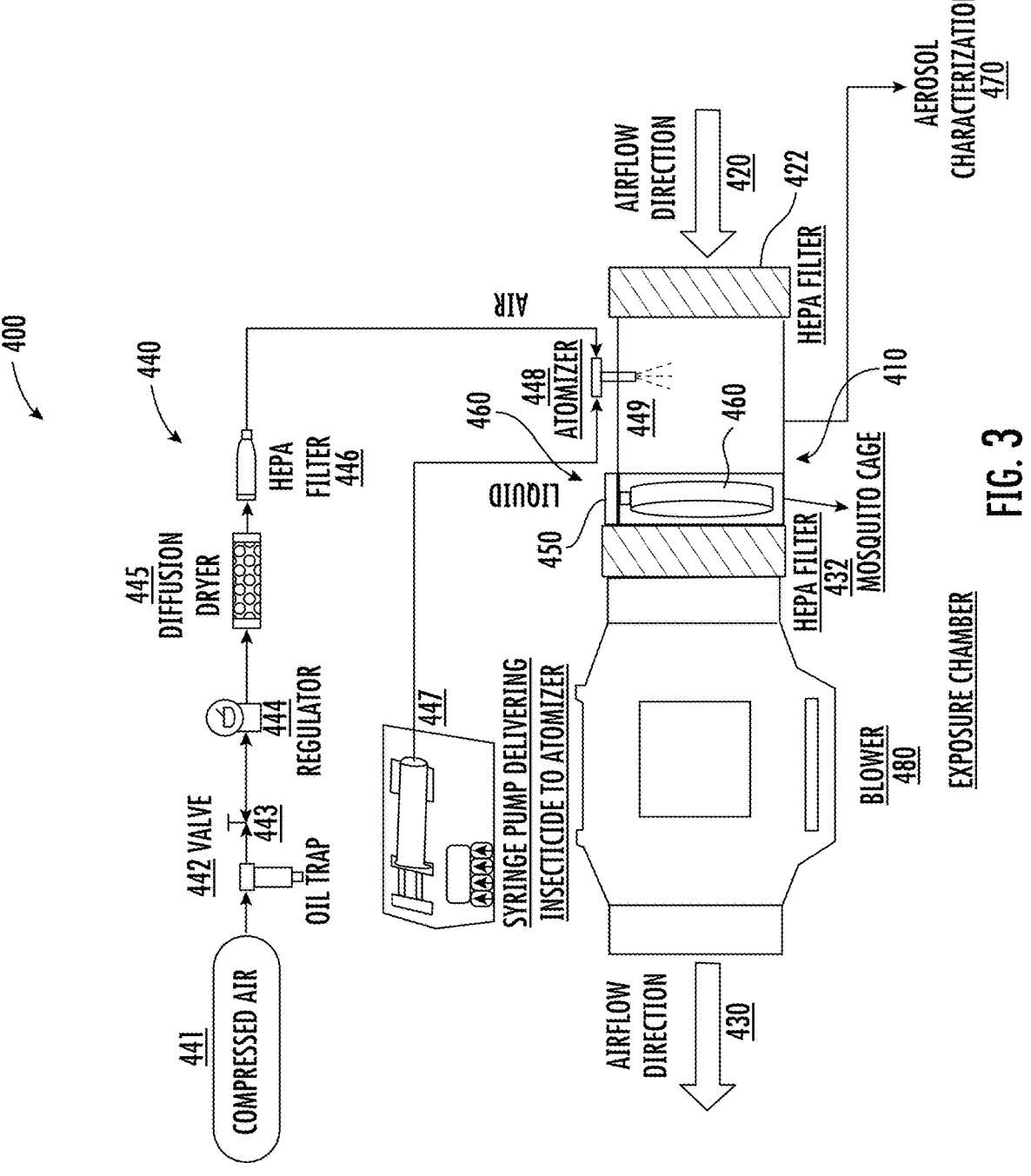
FIG. 3 is a schematic diagram of a wind tunnel system according to some embodiments.

As illustrated in FIGS. 3-4, the insect container holder 450 includes a housing 454 with a door 456 and an opening 458 that extends through the housing 454 (FIG. 4). A magnet 452 is on the door 456 of the housing 454 and is configured to connect to the insect container 460. The opening 458 of the holder 450 connects and allows gas/air to flow from the container through the outlet filter 432 (FIG. 3). In this configuration, the insect container 460 may be added to the chamber 410 by opening the door 456 and connecting the container 460 to the magnet 452 with a corresponding magnet 462 on the container 460. For example, the door 456 may include a hinge and is configured to pivot around the hinge between an open and a closed position. When in the closed position, the door 456 and the housing 454 are sealed to the outside and hold the insect container 460 in the wind tunnel chamber 410. In this configuration, insect containers 450 may be removed or added to the chamber 410.

Embodiments according to the present inventive concept will now be described with reference to the following non-limiting examples.

Examples

A method for exposing mosquitoes to FP using a novel compact wind tunnel is described. Initial wind tunnel testing was conducted on *Aedes albopictus* and *Culex pipiens/quinquefasciatus* lab and field colonies. Mosquitoes in 15 cm diameter cages were exposed to Biomist® 3+15 (FP with permethrin AI) or air (control) for 10 s within a compact wind tunnel (30 cm length). Immediately after exposure, mosquitoes from each group were transferred to separate 0.5 L cardboard cages, provided 20% sucrose, and placed in a 28° C. incubator with 14 h light: 10 h dark. Separate mosquitoes from the same populations were also exposed to permethrin AI in CDC bottle bioassays. Mortality was monitored/recorded for all groups 15, 30, 60, and 120 min post-exposure. Chi square tests ($P<0.05$) showed significantly higher mortality in *Aedes* compared to *Culex* populations for most time points in both the bottle bioassay and wind tunnel exposure experiments. As expected, mosquitoes exposed to Biomist® 3+15 in the wind tunnel showed higher mortality rates than bottle bioassay exposure to permethrin. Two *Culex* colonies classified as resistant to permethrin in bottle bioassays were susceptible to Biomist® 3+15 in the wind tunnel.

The compact wind tunnel is a laboratory alternative to potentially costly field trials that test FP efficacy, thereby avoiding factors such as unpredictable weather events, complex logistical planning, extended personnel hours. The wind tunnel developed here would allow mosquito control programs (MCP) to test efficacy of multiple FP several times during the year which might not be possible in field trials. The compact wind tunnel developed and tested here could be used by MCP across the United States and elsewhere to support their use of FP, resulting in more efficient mosquito control. Comparisons of different insecticide exposure methods is expected to provide practical information to MCP for operational decisions.

1. Introduction

Mosquitoes can develop resistance to insecticide active ingredients (AI) over time (Richards et al. 2020, 2022). Insecticide resistance (IR) is a public health issue as insecticides are one tool in an integrated mosquito management approach for suppressing nuisance mosquitoes and mosquito-borne diseases. Mosquito exposure to insecticides during ultra-low volume (ULV) space spray applications occurs via direct liquid contact to adulticide formulated products (FP) containing AI and other ingredients. The Centers for Disease Control and Prevention (CDC) bottle bioassay is a common method for assessing IR to AI in mosquitoes via exposure to dried residual AI (CDC 2013, 2019) and is considered a starting point for identifying resistance. Resistance to an AI does not necessarily indicate failure of a FP containing that AI since FP have additional ingredients (e.g., synergists) that enhance effectiveness (Burgess et al. 2022). Hence, assessing FP efficacy in a wind tunnel or field trial provides additional data for mosquito control programs (MCP) to make operational decisions.

A global study showed that IR management is lacking in regions such as Asia-Pacific, Latin America, and Caribbean due to factors such as lack of IR management plans, weak monitoring systems/databases, and/or lack of access to insecticides from different classes (van den Berg et al. 2021). There is widespread resistance to pyrethroids globally, but limited tracking is in place to address this problem (van den Berg et al. 2021). Two action pillars of the "Global vector control response 2017-2030" plan of the World Health Organization (WHO) are: 1) Enhance vector surveillance and monitoring/evaluation of interventions and 2) Scale up and integrate tools and approaches (WHO 2017).

The National Association of County and City Health Officials (NACCHO) surveyed 1,906 MCP in the United States (US) (53% health department, 20% MCP, 27% other department) (NACCHO 2017). Health departments, MCP, and other departments, were respectively 90, 65, and 87% classified as "needs improvement" with 98% of those lacking the capability or capacity to do IR testing (NACCHO 2017). It is likely only medium- to large-scale MCP would have the budget and personnel for evaluating IR to AI (e.g., CDC bottle bioassay) or FP using currently available methods (e.g., field trials, large-scale wind tunnels). However, small MCP could contract with larger/regional programs to have mosquitoes tested. It is unknown how many US or global MCP assess FP efficacy in mosquitoes.

Ground- and/or aerial-based ULV-applied field trials require a high degree of planning and coordination with personnel and can only be performed in appropriate weather conditions (i.e., no rain, low wind) during periods when mosquitoes are active. A program independently running a field trial can spend ca. $20,000 including items such as tripods, impingers, DropVision software (https://leateam-.com/product/dropvision/), hardware (e.g., microscope, camera, computer), slides for impinger, equipment for weather readings, tools for measuring distance, mosquito aspirators, and other items. This cost estimate does not include items such as personnel costs, field trial cages, mosquitoes, recurring annual fee ($1,200) for Drop Vision software. It is expected that many MCP do not carry out field trials unless facilitated by an industry partner having appropriate equipment and expertise.

The efficacy of insecticide delivery to the target is dependent on droplet size, movement in the air, and deposition (Matthews 1975; Scheff et al. 2019). Dispersion of insecticides in the air is commonly measured and reported as droplet size and smaller particles tend to drift further and may not impact the insect cuticle. A common method for reporting droplet size is volume median diameter (VMD) (i.e., droplet diameter where half of the droplet volume is smaller, and half is larger than the median diameter) (Pesticide Environmental Stewardship 2023). However, due to high mass concentrations, some spray nozzles are not feasible in small-scale laboratory studies. Rather, small-scale systems use nebulizers and atomizers to aerosolize liquids solutions (Sousan et al. 2021; Chaaban et al. 2022; Streuber et al. 2022). The Blaustein Atomizing Modules (BLAM, CH Technologies, Westwood, New Jersey) atomizer is designed to efficiently aerosolize liquid solutions at high concentrations and produce relatively large particle sizes when used directly in the air stream without its accompanying jar (Danelli et al. 2021). Particles generated with the BLAM are usually measured by mass median diameter (MMD) (i.e., particle diameter where half of the aerosol mass is smaller, and half is larger than the median diameter) (Finlay and Darquenne 2020). MMD and VMD measurements can be performed using optical aerosol instruments that capture the particle size, including any layer of water that may surround the particle or droplet. However, MMD and VMD values are identical if the aerosol density is identical to the density of the solution used to generate the particles, which applies to liquid aerosols (Bianco et al. 2021).

It has been reported that the appropriate droplet sizes for use in ULV application of FP have VMD<20 µm (Bonds 2012). A study using scanning electron microscopy on mosquitoes that flew through ULV aerosolized FP had droplets with VMD from 2-16 µm on their wings and antennae (Lofgren et al. 1973). The target efficiency of a droplet depends on factors such as droplet size, but also the target (e.g., mosquito) and droplet relative velocity (May and Clifford 1967). Droplet sizes used in mosquito control can vary by application equipment, specific gravity of FP, targeted habitat including vegetative and other obstacles, atmospheric conditions, and other factors (Hoffman et al. 2007; Bonds et al. 2012). Based on the principles of Stoke's Law, the ideal VMD for ground-based ULV mosquito control is ca. 5-25 µm (Mount et al. 1996). This differs for aerial mosquito control which requires a larger size (i.e., VMD 25-35 µm) since there are additional factors such as aircraft turbulence and sedimentation needed to bring the droplets to ground level (Barber et al., 2008; Bonds 2012). Droplet sizes were tested via laser-diffraction droplet-sizing system for several hand-held sprayers applying either water- or oil-based FP and there was a wide range of VMD observed (i.e., 14.9-90.5 µm [water-based] and 11.7-92.4 µm [oil-based]) depending on the equipment used (Hoffmann et al. 2007). In the same study, a ULV Colt sprayer delivered FP at a VMD of 14.9-16.0 µm (Aqua-Reslin) and 14.1 µm (Anvil 10+10).

The EPA-approved label of Biomist® 3+15 indicates cold aerosol or non-thermal aerosol generators should apply this FP at a flow rate of 3-18 oz/min when driving 10 mph https://www.clarke.com/product/biomist-adulticide/). For ground-based ULV applications, the target VMD is 8-30 μm.

Published information on wind tunnels shows these large-scale devices (usually several feet long) can be used for mosquito-related applications such as repellent and/or attractant testing (Dekker and Carde 2011; Tauxe et al. 2013; Hinze et al. 2021). Limited published studies use wind tunnels for FP testing (Hoffmann et al. 2008; Fritz et al. 2010) and no known studies exist showing a compact wind tunnel like the one developed here. A study showed ca. 10-50 μm VMD droplets measured via HELOS laser diffraction system (solution was mineral oil and fluorescent dye) produced by a spray nozzle attached to an air compressor in a wind tunnel (>8 m length), with size depending on wind speed and different screens being tested (Hoffmann et al. 2018). A 9.8 m long wind tunnel was used to test penetration of an oil/dye solution through different mesh sizes with droplet sizes measured via HELOS laser diffraction system (Fritz et al. 2010). A study evaluating prallethrin, sumithrin, and piperonyl butoxide (PBO) exposed *Culex quinquefasciatus* to droplet sizes of 2.5-5 μm (measured via microscope with micrometer) via an airbrush in a wind tunnel (>2.5 m length) found most droplets landed on wings and legs of mosquitoes (Cooperband et al. 2010).

The current study describes development of an innovative compact wind tunnel to apply FP and assess efficacy in mosquitoes of public health importance (i.e., *Aedes albopictus* Skuse and *Culex pipiens quinquefasciatus* Say). These results are compared to the CDC bottle bioassay for assessing IR to AI. This study is unique in that no such compact wind tunnel has been developed and this could lead to additional MCP assessing FP efficacy. This would increase the numbers of mosquitoes being assessed, thereby enhancing targeted control. Here, the focus is comparing and evaluating methods for assessment of an oil-based FP (Biomist® 3+15; wind tunnel) and corresponding AI (permethrin; CDC bottle bioassay).

2. Materials and Methods

2.1 Development of Wind Tunnel Prototype

An innovative compact wind tunnel prototype was designed and constructed as illustrated in FIGS. 1-4. In the experiment described, the wind tunnel of FIGS. 1-3 was used. The wind tunnel, machined from polyvinyl chloride (PVC), is 30 cm long and 18 cm in diameter. However, it should be understood that other sizes and materials may be used. For example, the dimensions of the wind tunnel may be increased or decreased by 10%, 20% or 50% or more without departing from the scope of the present inventive concept. Any suitable rigid material may be used to form the wind tunnel chamber, including metals, elastomeric materials, etc. Both sides of the wind tunnel have detachable covers, for example, formed of the same material as the wind tunnel (e.g., PVC), secured with latches and O-rings to create easy, air-tight system access. Here, clean air (e.g., filtered air to reduce or remove particles or particle-free air) was supplied to the inlet ("background air in") of the chamber at 100 LPM (Liters per minute) using a mass flow controller (Alicat Scientific, Tucson, Arizona [AZ]). The flow rate in the wind tunnel was sustained via an optional vacuum pump (Welch-Ilmvac 2585B-50, Niles, Illinois) at the outlet controlled by a valve (SMC vacuum regulator, Yorba Linda, California) and the flow rate was measured by a mass flow meter (Alicat Scientific, Tucson, AZ). To sustain atmospheric conditions inside the wind tunnel, the inlet air was supplied from a small chamber including a HEPA filter (Global Life Sciences Solutions 0.2 μm PTFE, Buckinghamshire, United Kingdom) open to the atmosphere to remove excess air and relieve pressure. The BLAM aerosol generator was positioned directly through the wind tunnel at the entrance of the inlet air, so the device could generate aerosols directly to the inlet air and the aerosols may be transported throughout the wind tunnel interior. Six aerosol sampling locations were positioned at different distances along the length of the wind tunnel (5, 13.5, 23 cm from opening); three on the top (1, 2, 3) and three at the bottom (4, 5, 6). The sampling locations may be ports that are configured to remove an amount of gas/aerosol from the wind tunnel, and to transport a sample to a mass spectrometer or other analyzer to characterize the aerosol of the insecticide in the wind tunnel (e.g., droplet size, concentration, etc.). Wind tunnel relative humidity and temperature were measured at the outlet using a data logger (HOBO, Bourne, Massachusetts). The wind tunnel also included three magnets at three locations along the length (8, 18, 28 cm from opening) used to position and secure a mosquito cage in a location in the wind tunnel using corresponding magnets on the mosquito cage. However, any suitable fastener or holder may be used to place the mosquito cage in the wind tunnel. The wind tunnel was positioned inside a chemical hood during FP applications.

It should be understood that the wind tunnel may utilize any suitable air flow generation technique. The air inlet does not necessarily require an air flow controller such as the mass flow controller. In some embodiments, the air flow in the wind tunnel may be controlled at the outlet or at another air flow opening into the chamber. For example, a blower may be connected to the chamber to pull air through the chamber at a variable speed, such as up to 7 mph. The inlet and the outlet of the chamber may be fitted with filters, such as HEPA filters to support a clean air (at or near zero particle background air) and to remove contaminants at the outlet. Although one aerosol generator is illustrated, more than one aerosol generator (e.g., multiple BLAM aerosol generators) may be used, or in some embodiments, a 48-nozzle BLAM aerosol generator may be used to achieve a desired concentration of insecticide at desired or high velocities in the chamber. Thus, the compressed air/mass flow controller and vacuum pump/flow meter may be replaced with a blower to maintain the high velocity in the chamber.

In some embodiments, a controller may be in communication with or provided as part of the air source or mass flow controller and/or the vacuum pump to control the air flow in and out of the wind tunnel. In some embodiments, the controller may be in communication with the sampling locations 1-6 and/or a mass spectrometer or other analysis device and/or the aerosol generator to monitor and/or control the amount of aerosol input to the wind tunnel from the aerosol generator.

As illustrated in FIG. 2, panels A-D, the wind tunnel 200 is shown under a chemical hood: outside with syringe pump (FIG. 2, panel A), inside with aerosol generator and sampler (FIG. 2, panel B), and with a mosquito cage (insect container) positioned inside (FIG. 2, panels C-D). As illustrated, the mosquito cage is a cylinder shape with a mesh or air permeable net on at least one side to permit aerosolized insecticide to enter and to prevent mosquitoes from exiting.

2.2 Aerosol Generation and Measurement in Wind Tunnel

Aerosol testing was conducted in two steps, first with petroleum distillate (i.e., kerosene) and then with an undiluted Biomist® 3+15 (label specifies 3% permethrin, 15% piperonyl butoxide, 82% other ingredients, including petroleum distillate) (https://www.clarke.com/product/biomist-adulticide/). The BLAM was fed continuously with petroleum distillate or Biomist® 3+15 liquids via a 60-mL syringe by injection using a syringe pump (model NE-1000, New Era Pump Systems Inc., Farmingdale, New York) operated at 1.6 mL/min. The syringe injection rate controlled the aerosol/vapor concentration generated and sustained 4 LPM particle-free air used with the BLAM to aerosolize the liquids. Aerosol measurements were performed using a portable mini wide range aerosol spectrometer (MiniWRAS, Grimm Aerosol Technik, Ainring, Germany). The MiniWRAS measures 41 particle sizes and uses optics to measure particles larger than 0.25 μm and a corona charger for smaller particles. The MiniWRAS measured the aerosol size distribution at the six sampling locations in the wind tunnel every 1 min for a duration of 3 min/location. Since MMD and VMD values are identical if the aerosol density is identical to the density of the solution used to generate the particles (i.e., liquid aerosols such as Biomist® 3+15), hereafter the aerosol density is referred to as VMD.

2.3 Mosquito Exposure to Aerosolized FP in Wind Tunnel

Female mosquitoes (4-5 d old) were aspirated from a colony cage and transferred to 15 cm diameter disposable cardboard mosquito cages with mesh screen (N=12–22 mosquitoes in each of three replicate cages) that included a magnet for attachment to inner wall of the wind tunnel (Clarke Mosquito Control, Chicago, Illinois). Experiments were conducted with and without the vacuum pump. This information determined the most appropriate placement of the mosquito cage. The following mosquito populations were used for initial testing: 1) *Ae. albopictus*, $F_{48}$, Orleans Parish, Louisiana (LA), maintained in colony by Richards lab personnel 2) *Ae. albopictus*, $F_1$, Craven County, NC eggs collected by Craven County Health Department personnel, 3) *Ae. albopictus*, $F_0$, New Hanover County, North Carolina (NC) eggs collected by New Hanover County Health Department personnel, 4) *Cx. pipiens quinquefasciatus*, $F_{219}$, Johannesburg, South Africa, obtained through Biodefense and Emerging Infections (BEI) Resources Repository 5) *Cx. pipiens/quinquefasciatus*, $F_1$, New Hanover County, NC egg rafts collected by New Hanover County Health Department personnel, and 6) *Cx. pipiens/quinquefasciatus*, $F_1$, Pitt County, NC egg rafts collected by Richards lab personnel. The $F_0$ generation mosquitoes were collected from the field as eggs, reared to adults and used in experiments (Richards et al. 2017a). The $F_1$ generation mosquitoes were collected from the field and propagated for one generation in the laboratory to increase sample size using established methods (Richards et al. 2017a).

Based on initial aerosol analyses of Biomist® 3+15 in the compact wind tunnel, mosquito cages were affixed to the middle position (#2) inside the wind tunnel via magnet on both the wind tunnel and cage. For the initial method development experiment, mosquitoes were exposed to aerosolized Biomist® 3+15 at 1.6 mL/min for either 5, 10, or 15 s before further processing. Control groups were exposed to air for the same time intervals instead of FPs. After exposure, each group was chilled at −20° C. for 15-20 s and transferred to separate clean 0.5 L cardboard cages (10-15 mosquitoes/cage; 3 replicate cages/group). Mosquitoes were provided 20% sucrose and placed in a 28° C. incubator with 14 h light: 10 h dark. Mortality was monitored and recorded for all groups 30 min, 60 min, 120 min, and 24 h post-exposure. Mosquito cages were discarded after use and the wind tunnel was cleaned with acetone after each experiment.

2.4 Mosquito Exposure to Permethrin AI in CDC Bottle Bioassay

Separate mosquitoes from the same populations used in wind tunnel experiments were also used in bottle bioassays, except for *Ae. albopictus*, $F_1$, Craven County, NC that were used in wind tunnel but not bottle bioassays due to low sample size. Female mosquitoes (4-5 d old) were aspirated from colony cages, transferred to 500 mL glass Wheaton bottles (N=11-20 mosquitoes in each of three to four replicate bottles), and exposed constantly to technical grade permethrin AI residue (8 μg/mL) (Chem Service, Westchester, Pennsylvania) for a 120 min period using established CDC bottle bioassay methods and mortality was monitored/recorded at 0, 15, 30, 60, and 120 min (CDC 2013, 2019; Richards et al. 2017ab, 2019). Bottle bioassay control groups were transferred to clean bottles following the same established methods (CDC 2013, 2019; Richards et al. 2017ab, 2019). Diagnostic dose and diagnostic time (DT) were determined using susceptible populations of *Ae. albopictus* and *Cx. quinquefasciatus* (data not shown).

2.5 Graphical and Statistical Analysis

Bar graphs were created to show differences in mortality between mosquito populations and exposure methods over time. Chi square tests (P<0.05) were used to determine differences in mortality between groups (SAS Institute, Cary, NC).

3. Results 3.1 Wind Tunnel Schematic and Prototype

Mosquito results presented here are when the mosquito cage was positioned in the middle (18 cm from opening, 15.5 cm from aerosol generation point).

3.2 Aerosol Generation and Measurement in Wind Tunnel

Figure 6:
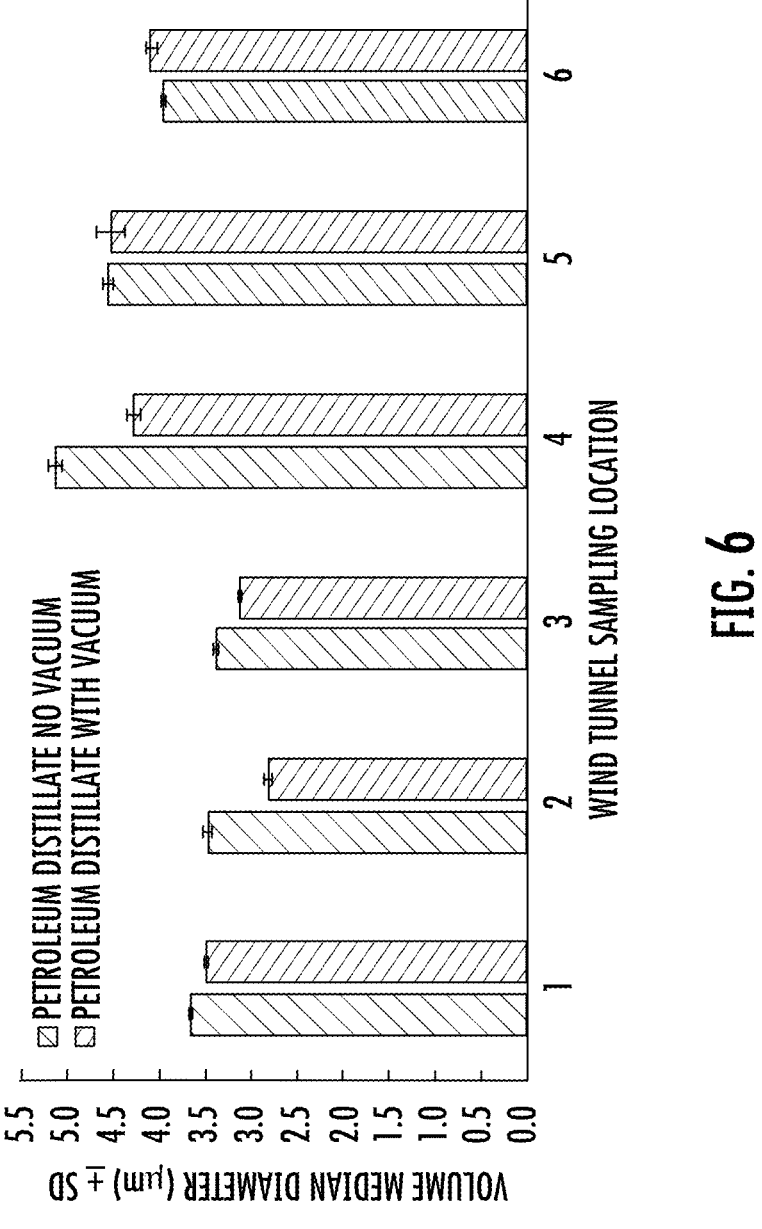
FIG. 6 is a bar graph of the particle volume median diameter of a petroleum distillate aerosolized in a wind tunnel system with and without a vacuum pump.
Figure 7:
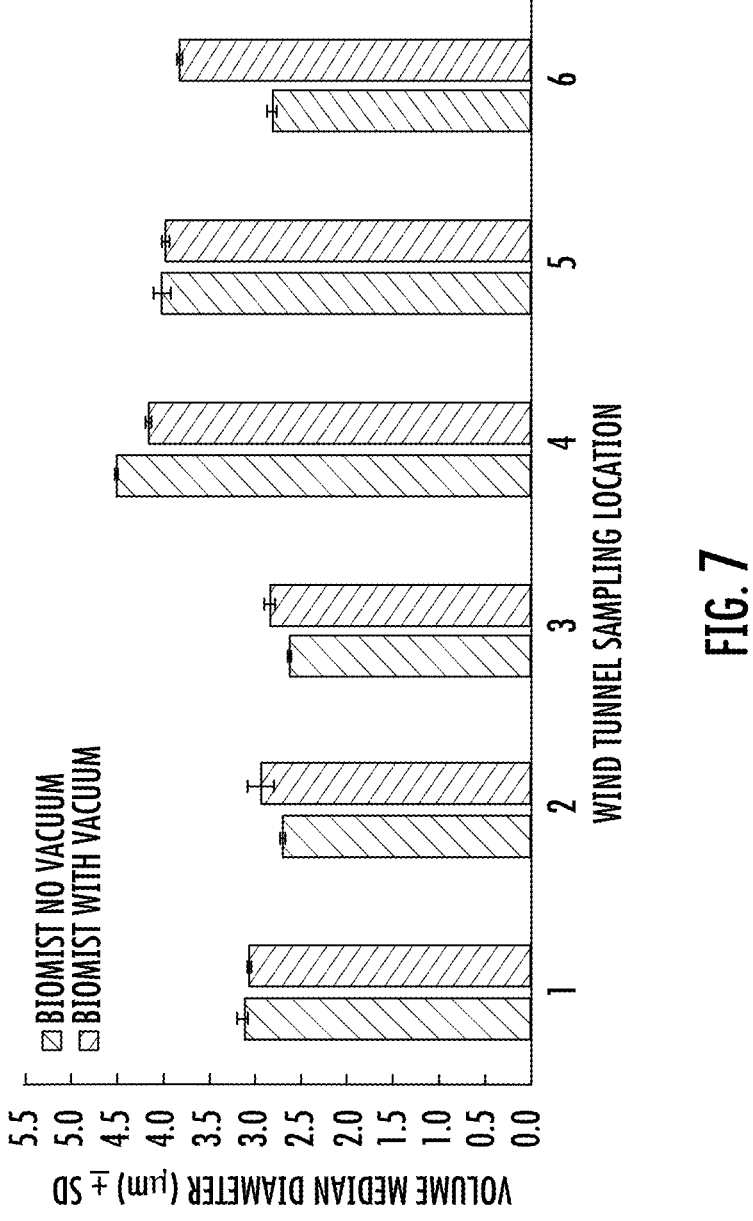
FIG. 7 is a bar graph of the particle volume median diameter of Biomist® 3+15 aerosolized in a wind tunnel system with and without Biomist® 3+15.

The temperature and relative humidity inside the chamber were 22.4° C. and 3.8% (±0.5). The VMD values measured with the MiniWRAS for the six sampling locations are shown in FIG. 6 (petroleum distillate) and FIG. 7 (Biomist® 3+15). For petroleum distillate, when the vacuum pump was off, VMD values ranged from 3.4-5.1 μm (mean=4.0 μm). The VMD values were larger for the bottom sampling positions compared to top positions. The VMD values when the vacuum pump was on were similar, i.e., values ranged from 2.8-4.5 μm (mean=3.7 μm). The standard deviation values of petroleum distillate measurements were similar for both vacuum settings (on/off) (range 0.01-0.15, mean=0.04). For Biomist® 3+15, when the vacuum pump was off, the VMD values ranged from 2.6-4.5 μm (mean=3.3 μm). The VMD values were larger for positions 4 and 5 (bottom), compared to positions 1-3 (top) and 6 (bottom). The VMD values when the vacuum pump was on were similar, i.e., values ranged from 2.9-4.2 μm (mean=3.5 μm), except that VMD at position 6 (bottom) was similar to positions 4 and 5 (bottom), with larger VMD values than the top locations. Standard deviation values for Biomist® 3+15 were similar for both vacuum settings (on/off) (range 0-0.14; mean=0.04). Based on these results, the middle position (sampling locations 2 and 5; VMD 3.5 μm) was chosen as the best location within the wind tunnel for the mosquito cage.

3.3 Mosquito exposure to FP in the Wind Tunnel

Initial method development steps included exposing the *Ae. albopictus* ($F_{48}$) colony to Biomist® 3+15 for 5, 10, or 15 s (data not shown) and mortality was measured at 15, 30, 60, 120 min, and 24 h post-exposure. Investigators determined the 10 s exposure time was appropriate (data not shown), hence that duration was used for other mosquito exposures and comparisons between mosquito populations. Mortality monitoring was concluded after 120 min. Mortality after 10 s wind tunnel exposure to Biomist® 3+15 was determined for: 1) *Ae. albopictus*, $F_{48}$, Orleans Parish, LA, 2) *Ae. albopictus*, $F_1$, Craven County, NC, 3) *Ae. albopictus*, $F_0$, New Hanover County, NC, 4) *Cx. pipiens quinquefasciatus*, $F_{219}$, Johannesburg, South Africa, 5) *Cx. pipiens/quinquefasciatus*, $F_1$, New Hanover County, NC, and 6) *Cx. pipiens/quinquefasciatus*, $F_1$, Pitt County, NC (FIG. 4). No mortality was observed in control groups. After a 10 s exposure to Biomist® 3+15, all mosquito populations were classified as susceptible (100% mortality at the last time point tested—120 min).

3.4 Mosquito Exposure to Permethrin AI in CDC Bottle Bioassay

Figure 8:
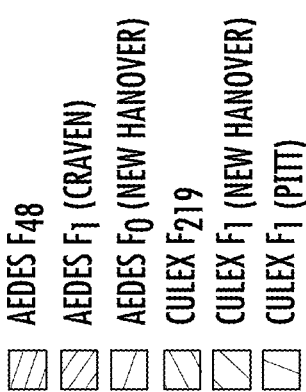
FIG. 8 is a bar graph of the mortality of types of mosquitoes in the wind tunnel system after exposure to Biomist® 3+15.
Figure 8:
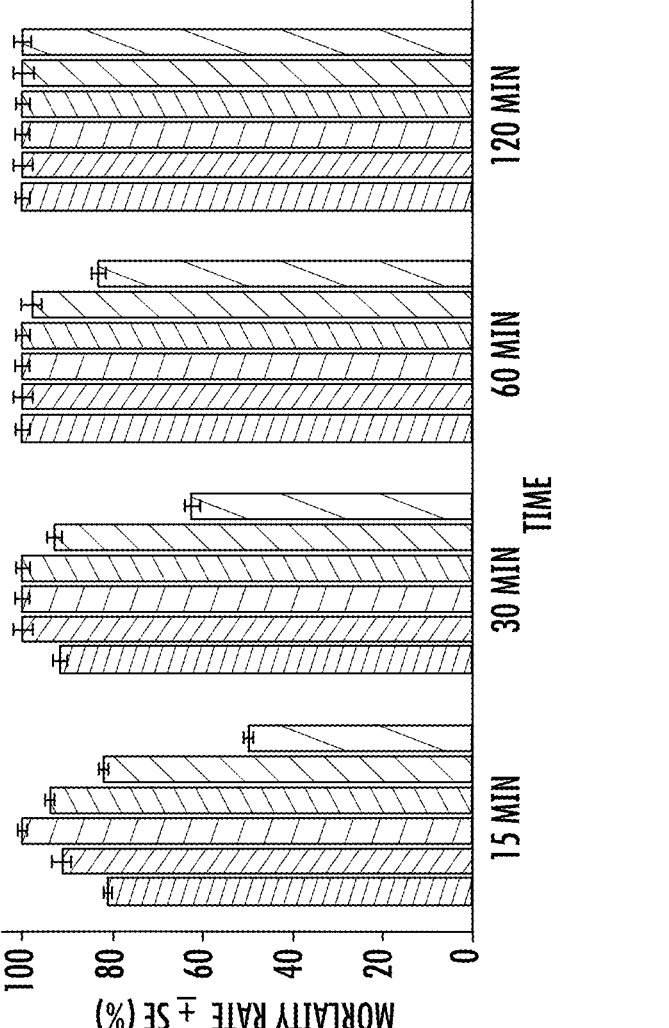
Figure 9:
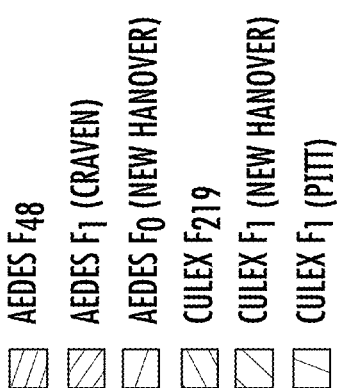
FIG. 9 is a bar graph of the mortality of types of mosquitoes in the wind tunnel during bioassay exposure to permethrin.
Figure 9:
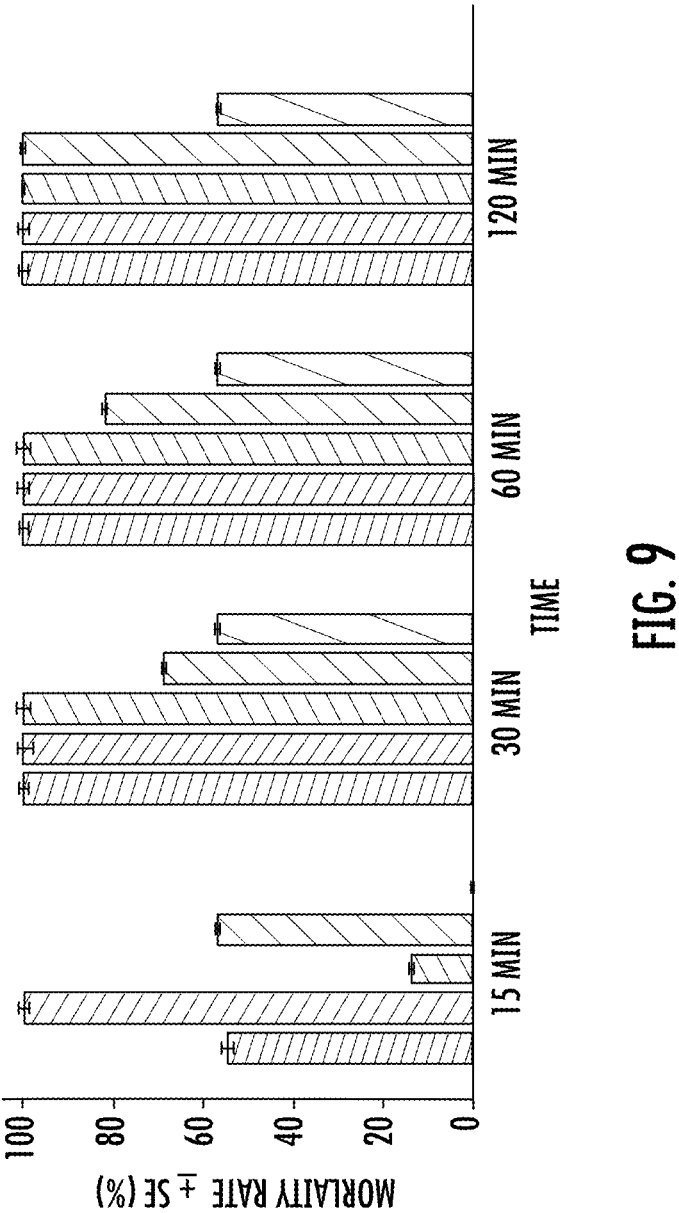

Female mosquitoes (4-5 d old) were aspirated from a separate colony cages, transferred to 500 mL glass Wheaton bottles, and exposed to AI residue using established CDC bottle bioassay methods and mortality was monitored/recorded at 15, 30, 60, and 120 min (FIG. 8). Bottle bioassay control groups were transferred to clean bottles following established methods (CDC 2013, 2019). At the 30 min DT for permethrin, *Ae. albopictus*, $F_{48}$, Orleans Parish, *Ae. albopictus*, $F_0$, New Hanover County, and *Cx. pipiens quinquefasciatus*, $F_{219}$, Johannesburg were classified as susceptible (100% mortality at the DT); however, *Cx. pipiens/quinquefasciatus*, $F_1$, New Hanover County (69% mortality) and *Cx. pipiens/quinquefasciatus*, $F_1$, Pitt County County (57% mortality) were classified as resistant. FIG. 9 is a bar graph of the mortality of types of mosquitoes in the wind tunnel during bioassay exposure to permethrin.

3.5 Statistical Analysis

Mortality was significantly higher in *Ae. albopictus* compared to *Cx. pipiens/quinquefasciatus* populations tested here 15 min ($\chi^2$=13.54, df=1, P=0.0002), 30 min ($\chi^2$=11.78, df=1, P=0.001) and 60 min ($\chi^2$=7.37, df=1, P=0.007) after wind tunnel exposure. Mortality was significantly higher in *Ae. albopictus* compared to *Cx. pipiens/quinquefasciatus* populations tested here at all time points during the bottle bioassay (15 min: $\chi^2$=75.72, df=1, P<0.0001; 30 min: $\chi^2$=39.83, df=1, P<0.0001; 60 min: x2=46.71, df=1, P<0.0001; 120 min: $\chi^2$=21.34, df=1, P<0.0001).

At 15 min ($\chi^2$=7.85, df=1, P=0.005), significant differences were observed in mortality rates in *Ae. albopictus* populations between wind tunnel and bottle bioassay exposures. *Culex pipiens/quinquefasciatus* populations showed significant differences in mortality between wind tunnel and bottle bioassay exposures at all time points (15 min: $\chi^2$=65.87, df=1, P<0.0001; 30 min: $\chi^2$=6.61, df=1, P=0.010; 60 min: $\chi^2$=28.55, df=1, P<0.0001; 120 min: $\chi^2$=23.24, df=1, P<0.0001), with rates generally higher in wind tunnel versus bottle bioassay.

4. Discussion 4.1 Practical Application of Compact Wind Tunnel

The compact wind tunnel successfully exposed mosquitoes to aerosolized oil-based FP Biomist® 3+15 for 10 s with particle sizes of ca. 3.3 μm (VMD) and resulted in 100% mortality in all mosquito populations tested. When the vacuum was off, particles larger than 3 μm in the wind tunnel settled due to gravity and were concentrated at the bottom sampling locations (positions 4 and 5). However, when the vacuum was on, there was a more uniform distribution of larger particles over the wind tunnel. These results indicate the vacuum should be on to ensure better particle distribution and constant airflow through the wind tunnel. The MMD values are assumed to be equal to VMD since the liquid aerosol generated has the same density as the Biomist® 3+15 solution. Typically, solid aerosols generated from liquid solutions, such as salt aerosols, do not have the same density as the original solution and take semi-spherical shapes. In contrast, the liquid particles generated from Biomist® 3+15 are spherical (Sousan et al. 2021). The 3.3 μm average VMD value measured in the current study is below the range stated by others as the ideal VMD for ground-based ULV mosquito control (i.e., ca. 5-25 μm) (Mount et al. 1996). This could be due to differences in detection technology between the MiniWRAS used here and other instruments and methods described in Mount et al. (1996) (e.g., Coulter® Counter-aerosols collected on media placed on chamber floor; Malvern® laser-aerosols pass through laser beam that measures variation in light intensity; microscopic measurement of slides waved through aerosol cloud). The MiniWRAS optics measure particle size, including any possible water layer on particles and does not differentiate between the two. Typically, particles are dried using hot air or silica gel before conducting aerosol measurements to ensure consistent measurements. This is done because any water layer that may be present has an inconsistent thickness, thereby potentially biasing aerosol size distribution since measurements might not be the same during each aerosol generation event. This was not necessary for the current study as particles were immediately measured upon aerosol generation.

The results that mortality was higher in wind tunnel exposed *Aedes* compared to *Culex* populations and at all time points in the bottle bioassay were expected since this trend has been previously observed in bottle bioassays (Richards et al. 2017ab, 2019). However, results here show that, although some populations (i.e., *Cx. pipiens/quinquefasciatus*, $F_1$, New Hanover County and Pitt County) were resistant to permethrin in the bottle bioassay, they were susceptible to Biomist® 3+15 in the wind tunnel, further illustrating that the bioassay should be used as a starting point for IR assessment since FP include additional ingredients (e.g., synergists) that can enhance effectiveness. This was also demonstrated in *Cx. pipiens* complex when five field populations were classified as resistant to the AI Sumethrin® (d-phenothrin), but three those five populations were classified as susceptible to Anvil® (FP containing sumethrin and PBO) (Burgess et al. 2022).

Continuing issues with IR in mosquito populations, difficulties (e.g., unpredictable weather, personnel time, logistical planning) and cost involved with caged mosquito field trials (Dzul-Manzanilla et al. 2019; Richards et al. 2022), large-scale wind tunnels that are not feasible for MCP make this new compact wind tunnel a tool that could benefit widespread MCP. Public agencies should consider becoming more active in routinely assessing IR in local mosquito populations during pre-emergency (e.g., disease prevention) situations. The wind tunnel could conceivably be used to test aerial and/or ground-based FP against any mosquito species, including flood water species to protect emergency workers after natural disasters, such as hurricanes (Brown et al. 2022) and additional FP will be tested in future studies. Strengthening tools to inform mosquito control operators about controlling mosquitoes, thereby preventing transmission of endemic and emerging mosquito-borne diseases is increasingly important to protect health.

The efficiency of testing mosquitoes in a compact wind tunnel could benefit medium- to large-scale MCP and allow a regional approach to FP testing for smaller programs who could consider delivering or mailing mosquitoes to the larger programs or universities for testing. The results here show the wind tunnel could help MCP, reducing personnel time and resources needed to assess the efficacy of FP against mosquitoes. Comparisons of different methods used for IR assessment will provide practical information to operators interested in assessing the relationship between AI IR and FP efficacy.

Although embodiments according to the present inventive concepts are described herein with respect to insecticides that are aerosolized in the wind tunnel and tested on mosquitoes, other insects, arachnids, and pests may be used to test the effectiveness of an agent.

5. Experimental Work

The current study uses the MiniWRAS to measure VMD values indirectly using MMD, unlike previous mosquito studies. Future wind tunnel work will focus on comparing the differences between the MiniWRAS and DC-IV Droplet system [KLD Labs, Hauppauge, New York] that is routinely used during calibration of ULV equipment used for FP applications. The flow rate here was lower than some previous studies and future experiments will be adjusted to reach higher flow rates comparable to previous work. Although 50-60% relative humidity was observed in the laboratory and during application of salt water during initial tests, application of oil-based products here lowered the humidity in the chamber. Although this likely did not impact mosquito mortality since they were in the wind tunnel for only 10 s, humidified air will be tested in future studies. Testing and comparison of oil- and water-based FP is also planned as part of the method development process and relative humidity will continue to be monitored with different types of FP. Ultraviolet dye will be used to determine droplet spread for each FP on mosquitoes in the wind tunnel. A future iteration of the wind tunnel prototype will also include testing of HEPA-filtered air out of the wind tunnel and this should also improve safety for applications outside of a chemical hood (i.e., outdoors) for programs not having access to a chemical hood. The compact wind tunnel is a proxy for field trials and could be used by programs not having the equipment or personnel time to coordinate and conduct field trials. Field conditions (i.e., wind, temperature, humidity, vegetation) may impact delivery of aerosolized FP to mosquitoes.

6. Conclusions

Only the most effective insecticides should be applied to control mosquitoes. Not all MCP utilize adulticides (e.g., they may only apply larvicides, conduct source reduction, and/or provide educational materials to the public). For programs that apply FP, ULV space spray treatments must be applied during appropriate meteorological conditions and when mosquitoes are actively flying. Tools for assessing mosquito IR and efficacy of FP could be improved in conjunction with informed messaging about the relationship between testing AI (e.g., bottle bioassay) and FP (e.g., wind tunnel, field trial) to help protect public health. The compact wind tunnel developed here could be used by multiple MCP. This device is a laboratory alternative to field trials that test FP efficacy, thereby avoiding factors such as weather events and personnel burdens (e.g., outside of normal business hours, weather dependent so may need to attempt repeatedly) associated with field trials. The current implementation of field trials can take days and several personnel and can be cancelled or delayed due to poor weather conditions.

Hence, a more streamlined approach using the compact wind tunnel could allow MCP to better serve the public by allowing for a more targeted approach. Wind tunnel assessments can be planned and executed in 1-2 days (not including mosquito propagation), thereby avoiding ca. 1-2 weeks of logistical preparation, expense, and execution involved in a field trial. The wind tunnel would allow programs to test efficacy of FP on local mosquitoes multiple times a year which might not be possible in field trials. The compact wind tunnel could potentially be used by US MCP and elsewhere. Comparisons of different insecticide exposure methods is expected to provide practical information for operators interested in analyzing the relationship between AI assessment of IR and FP efficacy.

REFERENCES

Barber J A S, Latham M, Greer M, Canopy effects droplets size distribution and meteorological change. *J Am Mosq Cont Assoc,* 24:177-181 (2008).

Bianco F, Salomone F, Milesi I, Murgia X, Bonelli S, Pasini E, Dellacà R, Ventura M L, Pillow J, Aerosol drug delivery to spontaneously-breathing preterm neonates: Lessons learned. *Respir Res* 22:71 (2021).

Bonds J A, Ultra-low volume space sprays in mosquito control: A critical review. *Med Vet Ent,* 26:121-130 (2012).

Brown J S, Byrd B D, Connelly C R, Richards S L, Operational insights into mosquito control disaster response in coastal North Carolina: Experiences with the Federal Emergency Management Agency after Hurricane Florence. *J Env Hlth,* 85:24-31 (2022).

Burgess E R 4th, Lopez K, Irwin P, Jaeger C P, Estep A S. Assessing pyrethroid resistance status in the *Culex pipiens* complex (Diptera: Culicidae) from the northwest suburbs of Chicago, Illinois using Cox regression of bottle bioassays and other detection tools. *PLOS One,* 17: e0268205 (2022).

Centers for Disease Control and Prevention. Parasites— CDC bottle bioassay [Internet]. 2013. Available: http://www.cdc.gov/parasites/education_training/lab/bottlebioassay.html Centers for Disease Control and Prevention. CONUS manual for evaluating insecticide resistance in mosquitoes using the CDC bottle bioassay kit [Internet]. 2019. Available: https://www.cdc.gov/zika/pdfs/CONUS-508.pdf Chaaban O, Balanay J A G, Sousan S, Assessment of best-selling respirators and masks: Do we have acceptable respiratory protection for the next pandemic? *Am J Inf Cont,* 51:388-395 (2022). Cooperband M F, Golden F V, Clark G G, Jany W, Allan S A. Prallethrin-induced excitation increases contact between sprayed ultralow volume droplets and flying mosquitoes (Diptera: Culicidae) in a wind tunnel. *J Med Entomol,* 47:1099-106 (2010).

Danelli, S G, Brunoldi M, Massabo D, Parodi F, Vernocchi V, Prati P, Comparative characterization of the performance of bio-aerosol nebulizers in connection with atmospheric simulation chambers. *Atmosph Meas Tech* 14:4461-4470 (2021).

Dekker T, Carde R T, Moment-to-moment flight manoeuvres of the female yellow female mosquito (*Aedes aegypti* L.) in response to plumes of carbon dioxide and human skin odour. *J Exp Biol,* 214:3480-3494 (2011).

Dzul-Manzanilla F, Correa-Morales F, Medina-Barreiro A, Bibiano-Marin W, Vadillo-Sanchez J, Riestra-Morales M, Del Castillo-Centeno L F, Moreles-Rios E, Martin-Park A, Gonzalez-Olvera G, Elizondo-Quiroga A E, Lenhart A, Vazquez-Prokapec G, Che-Mendoza A, Manrique-Saide P, Field efficacy trials of aerial ultra-low volume application of insecticides against caged *Aedes aegypti* in Mexico. *J Am Mosq Cont Assoc,* 35:140-146 (2019).

Finlay W H, Darquenne C (2020) Particle size distributions. *J Aeros Med Pulmon Drug Deliv,* 33, 178-180.

Fritz B K, Hoffmann W C, Farooq M, Walker T, Bonds J (2010) Filtration effects due to bioassay cage design and screen type. *J Am Mosq Cont Assoc,* 26:411-421 (2010).

Hinze A, Lantz J, Hill S R, Ignell R, Mosquito host seeking in 3D using a versatile climate-controlled wind tunnel system. *Front Behav Neurosci,* 15:643693 (2021).

Hoffmann W C, Walker T W, Smith V L, Martin D E, Fritz B K, Droplet size characterization of handheld atomization equipment typically used in vector control. *J Am Mosq Cont Assoc* 23:315-320 (2007).

Hoffmann W C, Fritz B K, Farooq M, Cooperband M F, Effects of wind speed on aerosol spray penetration in adult mosquito bioassay cages. *J Am Mosq Cont Assoc* 24:419-426 (2008).

Lofgren C S, Anthony D W, Mount G A, Size of aerosol droplets impinging on mosquitoes as determined with a scanning electron microscope. *J Econ Ent* 66:1085-1088 (1973).

Matthews G A, Determination of droplet size. PANS Pest Art News Summ 21:213-225 (1975).

May K R, Clifford R, The impaction of aerosol particles, spheres ribbons and discs. *Ann Occup Hyg,* 10:83-95 (1967).

Mount G A, Biery T L, Haile D G, A review of ultra low volume aerial sprays of insecticide for mosquito control. *J Am Mosq Cont Assoc,* 12:601-618 (1996).

National Association of County and City Health Officials [Internet]. 2017. Mosquito control capabilities in the United States. Available: https://www.naccho.org/up-loads/downloadable-resources/Mosquito-control-in-the-U.S.-Report.pdf Pesticide Environmental Stewardship, Understanding droplet sizes [Internet]. 2019. Available: https://pesticidestew-ardship.org/pesticide-drift/understanding-droplet-size/

Richards S L, Balanay J G, Fields M, and K Vandock (2017a) Baseline insecticide susceptibility screening against six active ingredients for *Aedes* and *Culex* (Diptera: Culicidae) mosquito populations. Journal of Medical Entomology 54 (3): 682-695.

Richards S L, Balanay J G, White A V, Hope J, Vandock K, Byrd B D, Reiskind M H, Insecticide susceptibility screening against *Culex* and *Aedes* (Diptera: Culicidae) mosquitoes from the United States. *J Med Ent* 55:398-407 (2017b).

Richards S L, Byrd B D, Reiskind M H, White A V, Insecticide resistance profiles of North Carolina *Aedes albopictus* for active ingredients and formulated products, 2017. *J Med Ent* 56:761-773 (2019).

Richards S L, Byrd B D, Reiskind M H, White A V, Assessing insecticide resistance in adult mosquitoes: Perspectives on current methods. *Env Hlth Ins* 14:1-7 (2020).

Richards S L, Byrd B D, Breidenbaugh M, Vandock K, Survey of United States mosquito control programs reveals opportunities to improve the operational value of Centers for Disease Control and Prevention bottle bioassays. *J Med Ent* 59:1827-1830 (2022).

Scheff D S, Brabec D, Campbell J F, Arthur F H, Case study: A practical application of an aerosol treatment in a commercial mill. *Insects* 10:150 (2019).

Sousan S, Regmi S, Park Y M. Laboratory evaluation of low-cost optical particle counters for environmental and occupational exposures. *SEN* 21::4146 (2021).

Streuber D, Park Y M, Sousan S, Laboratory and field evaluations of the GeoAir2 air quality monitor for use in indoor environments. *Aer Air Qual Res* 22:220119 (2022).

Tauxe G M, Mac William D, Boyle S M, Guda T, Ray A, Targeting a dual detector of skin and $CO_2$ to modify mosquito host seeking. *Cell* 155:1365-1379 (2013).

van den Berg H, da Silva Bezerra H S, Al-Eryani S, Chanda E, Nagpal B N, Knox T B, Velayudhan R, Yadav R S. Recent trends in global insecticide use for disease vector control and potential implications for resistance management. *Scientific Reports* 11:23867 (2021).

World Health Organization. Global vector control response 2017-2030 [Internet]. 2017. Available: https://www.who.int/publications/i/item/9789241512978#cms Zhang H, Dorr G J, Hewitt A J, Retention and efficacy of ultra-low volume pesticide applications on *Culex quinquefasciatus* (Diptera: Culicidae). *Env Sci Poll Res* 22:16492-16501 (2015).

The foregoing is illustrative of the present inventive concept and is not to be construed as limiting thereof. Although a few example embodiments have been described, those skilled in the art will readily appreciate that many modifications are possible in the exemplary embodiments without materially departing from the novel teachings of this inventive concept. Accordingly, all such modifications are intended to be included within the scope of this inventive concept as defined in the claims. Therefore, it is to be understood that the foregoing is illustrative of the present inventive concept and is not to be construed as limited to the specific embodiments disclosed, and that modifications to the disclosed embodiments, as well as other embodiments, are intended to be included within the scope of the appended claims.

What is claimed is:

1. A wind tunnel system configured to assess insecticides, the system comprising:
   a chamber having an inlet configured to receive a gas flowing into the chamber and an outlet configured to output the gas from the chamber;
   an inlet filter configured to filter the gas flowing into the chamber;
   an outlet filter configured to filter the gas flowing out of the chamber;
   an aerosol generator configured to generate an insecticide aerosol downstream from the inlet filter;
   an insect container holder configured to secure an insect container in the chamber downstream from the aerosol generator and upstream from the outlet filter; and
   an airflow controller configured to flow the gas into the inlet and out of the outlet of the chamber such that the insecticide aerosol flows through an insect container in the chamber.

2. The wind tunnel system of claim 1, further comprising an insect container configured to releasably connect to the insect container holder, the insect container comprising a gas permeable sidewall configured to allow the gas to flow through the housing.

3. The wind tunnel system of claim 2, wherein the insect container holder comprises a magnet on an interior surface of the chamber, and the insect container comprises a corresponding magnet configured to secure the insect container to the magnet on the interior surface of the chamber.

4. The wind tunnel system of claim 1, wherein the insect container holder further comprises a housing and a door connected to the housing, and a connector on the door such that when the door is in the open position, the connector is exposed and is configured to receive the insect container thereon, and when the door is in the closed position, the connector and, optionally, the insect container secured by the insect container holder, is positioned upstream of the inlet.

5. The wind tunnel system of claim 4, wherein the door further comprises a seal between the door housing.

6. The wind tunnel system of claim 1, wherein the airflow controller comprises a blower.

7. The wind tunnel system of claim 6, wherein the blower is downstream of the outlet filter.

8. The wind tunnel system of claim 1, wherein the airflow controller comprises a mass flow controller configured to control the flow of the gas in the chamber.

9. The wind tunnel system of claim 8, wherein the airflow controller further comprises a vacuum pump flow meter downstream of the insect container holder, and wherein the mass flow controller is upstream of the insect container holder.

10. The wind tunnel system of claim 1, further comprising a sampling device configured to characterize the aerosolized insecticide.

11. The wind tunnel system of claim 1, wherein the insect container is configured to test mosquitoes.

12. A method of assessing insecticide with a wind tunnel system, the method comprising:

providing a wind tunnel system comprising:

a chamber having an inlet configured to receive a gas flowing into the chamber and an outlet configured to output the gas from the chamber;

an inlet filter configured to filter the gas flowing into the chamber;

an outlet filter configured to filter the gas flowing out of the chamber;

an aerosol generator configured to generate an insecticide aerosol downstream from the inlet filter;

an insect container holder configured to secure an insect container in the chamber downstream from the aerosol generator and upstream from the outlet filter; and an airflow controller configured to flow the gas into the inlet and out of the outlet of the chamber;

connecting an insect container to the insect container holder, the insect container comprising a gas permeable sidewall configured to allow the gas to flow through the insect container;

aerosolizing insecticide in the chamber; and flowing gas through the inlet and out of the outlet of the chamber such that the insecticide aerosol flows through an insect container in the chamber.

13. The method of claim 12, further comprising securing the insect container in the chamber with a pair of cooperating magnets.

14. The method of claim 12, wherein the insect container holder further comprises a housing and a door connected to the housing, and a connector on the door, the method further comprising: opening the door and connecting the insect container to the connector, and closing the door such that the insect container secured by the insect container holder is positioned upstream of the inlet.

15. The method of claim 14, wherein the door further comprises a seal between the door housing.

16. The method of claim 12, wherein the airflow controller comprises a blower and the step of flowing gas is performed with the blower.

17. The method of claim 16, wherein the blower is downstream of the outlet filter.

18. The method of claim 12, wherein the airflow controller comprises a mass flow controller and the step of flowing gas is performed with the mass flow controller to control the flow of the gas in the chamber.

19. The method of claim 18, wherein the airflow controller further comprises a vacuum pump flow meter downstream of the insect container holder, and wherein the mass flow controller is upstream of the insect container holder.

20. The method of claim 12, further comprising sampling the aerosolized insecticide in the chamber and characterizing the aerosolized insecticide.

21. The method of claim 12, wherein the insects in the insect container are mosquitoes.

* * * * *